United States Patent [19]

Nakao et al.

[11] Patent Number: 5,290,915
[45] Date of Patent: * Mar. 1, 1994

[54] PLACENTA-DERIVED COAGULATION INHIBITOR

[75] Inventors: Hiroshi Nakao, Ibaraki; Takao Nagoya, Tokorozawa; Yushi Saino, Tokyo; Masahiro Maki, Akita; Hideo Tani, Kodaira, all of Japan

[73] Assignee: Kowa Co., Ltd., Nagoya, Japan

[*] Notice: The portion of the term of this patent subsequent to Mar. 2, 2005 has been disclaimed.

[21] Appl. No.: 820,004

[22] Filed: Jan. 13, 1992

Related U.S. Application Data

[63] Continuation of Ser. No. 116,908, Nov. 5, 1987, Pat. No. 5,192,694.

[30] Foreign Application Priority Data

Nov. 14, 1986 [JP] Japan .................... 61-269588

[51] Int. Cl.$^5$ .................... C07K 15/06; A61K 37/24
[52] U.S. Cl. .................... 530/350; 530/851
[58] Field of Search .................... 530/350, 851; 514/12

[56] References Cited

U.S. PATENT DOCUMENTS

| 4,301,064 | 11/1981 | Bohn . | |
|---|---|---|---|
| 4,507,229 | 5/1985 | Bohn . | |
| 4,732,891 | 3/1988 | Maki et al. | 530/350 X |
| 4,937,324 | 6/1990 | Fujikawa et al. . | |

FOREIGN PATENT DOCUMENTS

WO88/05659 8/1988 PCT Int'l Appl. .

OTHER PUBLICATIONS

J. Biochem. 102,1261–1273 (1987), Iwasaki et al.
Suggs et al, "Use of synthetic oligonucleotides as hybridization probes: Isolation of cloned cDNA sequences for human beta$_2$-microglobulin*", Proc. Natl. Acad. Sci. USA, vol. 78, No. 11, pp. 6613–6617, Nov. 1981, Biochemistry.
Young et al, "Efficient isolation of genes by using antibody probes", Proc. Natl. Acad. Sci. USA, vol. 80, pp. 1194–1198, Mar. 1983, Biochemistry.
Iwasaki et al, "Structure and Expression of cDNA for Calphobindin II, a Human Placental Coagulation Inhibitor", J. Biochem., 106, 43–49, 1989.
Funakoshi et al, "Human Placental Anticoagulant Protein: Isolation and Characterization", Biochemistry, vol. 26, No. 17, Aug. 25, 1987, pp. 5572–5578.

Primary Examiner—Howard E. Schain
Attorney, Agent, or Firm—Oblon, Spivak, McClelland, Maier & Neustadt

[57] ABSTRACT

A monoclonal antibody specific to a human placenta-derived coagulation inhibitor is disclosed. The antibody is produced by culturing a hybridoma which secretes it. A human placenta-derived coagulation inhibitor can be purified by using the monoclonal antibody as an immunoadsorbent. The human placenta-derived coagulation inhibitor can be immunologically assayed by using the monoclonal antibodies.

1 Claim, 2 Drawing Sheets

PLACENTA-DERIVED COAGULATION INHIBITOR

This is a continuation of application Ser. No. 07/116,908, filed on Nov. 5, 1987, now U.S. Pat. No. 5,192,694.

BACKGROUND OF THE INVENTION:

i) Field of the Invention

This invention relates to a monoclonal antibody specific to a substance derived and purified from a human placenta and having anticoagulant activity (hereinafter abbreviated as "PCI"), a hybridoma secreting the monoclonal antibody, and utilization of the monoclonal antibody.

ii) Description of the Prior Art

The cell fusion technology has been developed rapidly since the report of Keller and Milstein [Nature, 495-497 (1975)]. It has been known that a hybridoma obtained by fusing mammalian spleen cells and myeloma cells secretes various antibodies depending on the characteristics of the spleen cells employed. It has also been attempted to form a hybridoma, which secretes a monoclonal antibody against various biological substances such as proteins and hormones, by effecting cloning based on the characteristics of the hybridoma and also to secrete the monoclonal antibody [E. Dale Servier et al., Clinical Chemistry, 27(11), 1797-1806 (1981)]. In the meantime, the present applicant previously succeeded in isolating and purifying a substance having anticoagulant activity (PCI) from a human placenta and applied for a patent thereon (European Patent Application Publication No. 0217341). PCI is a substance which has the following properties and is useful as a medicine.

(1) Molecular weight (SDS-polyacrylamide gel electrophoresis, reduced state): 34,000 ±2,000.
(2) Isoelectric point (isoelectric column electrophoresis using an ampholyte): 4.7 ±0.1.
(3) Stability:
  (a) Inactivated by a heat treatment at 50° C. for 30 minutes.
  (b) Stable in a pH range of 4-10.
  (c) Stable in plasma at 37° C. for 30 minutes.
(4) Effects:
  (a) Capable of prolonging the recalcification time.
  (b) Capable of prolonging the prothrombin time.
  (c) Capable of prolonging the activated partial thromboplastin time.
(5) Analysis of amino acids: The existence of aspartic acid, threonine, serine, glutamic acid, proline, glycine, alanine, ½ cystine, valine, methionine, isoleucine, leucine, tyrosine, phenylalanine, histidine, lysine and arginine is recognized by the analysis of amino acids.

One example of preparation of PCI will be described subsequently in Example 1. It may be summarized as follows.

A placenta homogenate is first prepared from the human placenta and then subjected to centrifugation. The homogenization is effected in the following manner. After cutting off the amnion and the like from the placenta, the placenta is washed thoroughly with a physiological saline, followed by homogenization by the use of a Waring blender and "Polytron" (trade mark; manufactured by Kinema SA). The thus-obtained homogenate was subjected to centrifugation, thereby obtaining a supernatant and sediment. The resulting placenta homogenate sediment is washed thoroughly with a buffer and is then subjected again to centrifugation to obtain a washed sediment, followed by extraction. Namely, the thus-obtained sediment of the placenta homogenate is immersed in a buffer, which contains a chelating agent such as EDTA, EGTA, oxalic acid, citric acid, sodium nitrilotriacetate or phosphoric acid, and/or another buffer containing a surfactant such as "Triton X-100", Lubrol (trade mark), SDS, deoxycholic acid or the like. After allowing it to stand overnight at 4° C.-8° C., the mixture is centrifuged to collect a supernatant as an extract. Here, the extraction may be carried out by using both chelating agent and a surfactant.

The supernatant is subjected further to ultracentrifugation at 50,000 to 100,000 × g to obtain a microsome fraction as a sediment. After washing the microsome fraction, it was extracted with a chelating agent and/or a surfactant in the same manner as described above and the resultant extract was subjected to ultracentrifugation to collect a supernatant as an extract.

The thus-obtained extract is subjected to ammonium sulfate fractionation. The ammonium sulfate fractionation is effected in the following manner. First, solid ammonium sulfate is added to 35% of its saturated concentration to the extract, followed by centrifugation to collect a supernatant. Ammonium sulfate is then added to the supernatant until its concentration reached 85% of its saturated concentration, followed by centrifugation to collect a sediment.

The resulting ammonium sulfate fraction is then purified by known isolation and purification procedures including, for example, dialysis, ion exchange chromatography, gel filtration, adsorption chromatography, hydrophobic chromatography, isoelectric point column electrophoresis, affinity chromatography using lectin or an antibody, and the like either singly or in combination, thereby obtaining PCI. For example, a fraction obtained by subjecting the chelating agent and/or surfactant extract to ammonium sulfate fractionation is dialyzed thoroughly. The resulting dialyzate is then eluted in accordance with the linear concentration gradient method in which "DEAE-Toyopearl" (trade name) is used. After an active fraction thus obtained is dialyzed, it is caused to pass through "Blue Sepharose" (trade name; product of Pharmacia AB). The active fraction is then concentrated and subjected to gel filtration through "Sephadex G-100" (trade name; product of Pharmacia AB), thereby to obtain PCI.

PCI is however contained only in a trace amount in the placenta, and no sufficient specific binding is established with PCI in various chromatographic techniques which are employed routinely. It is hence difficult to obtain PCI in a highly pure form. Moreover, such conventional procedures require many steps and are unable to achieve any satisfactory recovery rate.

It has therefore been desired to develop a specific purification process for obtaining high-purity PCI easily at a high recovery rate. In order to use PCI as an anticoagulant, it has also been desired to elucidate the mechanism of the action of PCI and further to develop a high-sensitivity assay for PCI as a method for measuring its blood level.

SUMMARY OF THE INVENTION

The present inventors have carried out an extensive investigation with a view toward solving these problems. As a result, it has been succeeded to obtain by a cell fusion technique a hybridoma secreting a monoclonal antibody specific to PCI. It has also been found that the monoclonal antibody specific to PCI can be obtained using the hybridoma and the use of the monoclonal antibody permits high level purification and immunoassay of PCI, thereby leading to completion of this invention.

The present invention therefore provides a monoclonal antibody specific to PCI, a hybridoma secreting the monoclonal antibody, a purification process of PCI featuring the use of the monoclonal antibody as an immunoadsorbent, as well as an immunoassay of PCI featuring the use of the monoclonal antibodies.

The hybridoma of this invention secretes a monoclonal antibody specific to PCI. Use of the monoclonal antibody then makes it possible to simplify the isolation and purification process of PCI, so that PCI of extremely high purity can be obtained at a high recovery rate. Moreover, the solid carrier with the monoclonal antibody coupled thereon is usable repeatedly provided that it is washed. The antibody-coupled carrier is extremely useful from the industrial viewpoint, since its use can simplify the purification step and moreover, is economical.

Further, the anti-PCI monoclonal antibody of this invention can also be used for the immunoassay of PCI in the treatment of abnormality or a disease in the coagulative fibrinolysis system of blood.

BRIEF DESCRIPTION OF THE DRAWINGS

The above and other objects, features and advantages of the present invention will become apparent from the following description and the appended claims, taken in conjunction with the accompanying drawings, in which:

FIG. 1: PCI-A46 and 176 were used separately as coating monoclonal antibodies, while PCI-A180 was used commonly as a monoclonal antibody to be conjugated.

FIG. 2: PCI-A46 was used commonly as a coating monoclonal antibody, whereas PCI-A39, 169 and 176 were employed separately as monoclonal antibodies to be conjugated.

DETAILED DESCRIPTION OF THE INVENTION AND PREFERRED EMBODIMENTS

Figure 1:
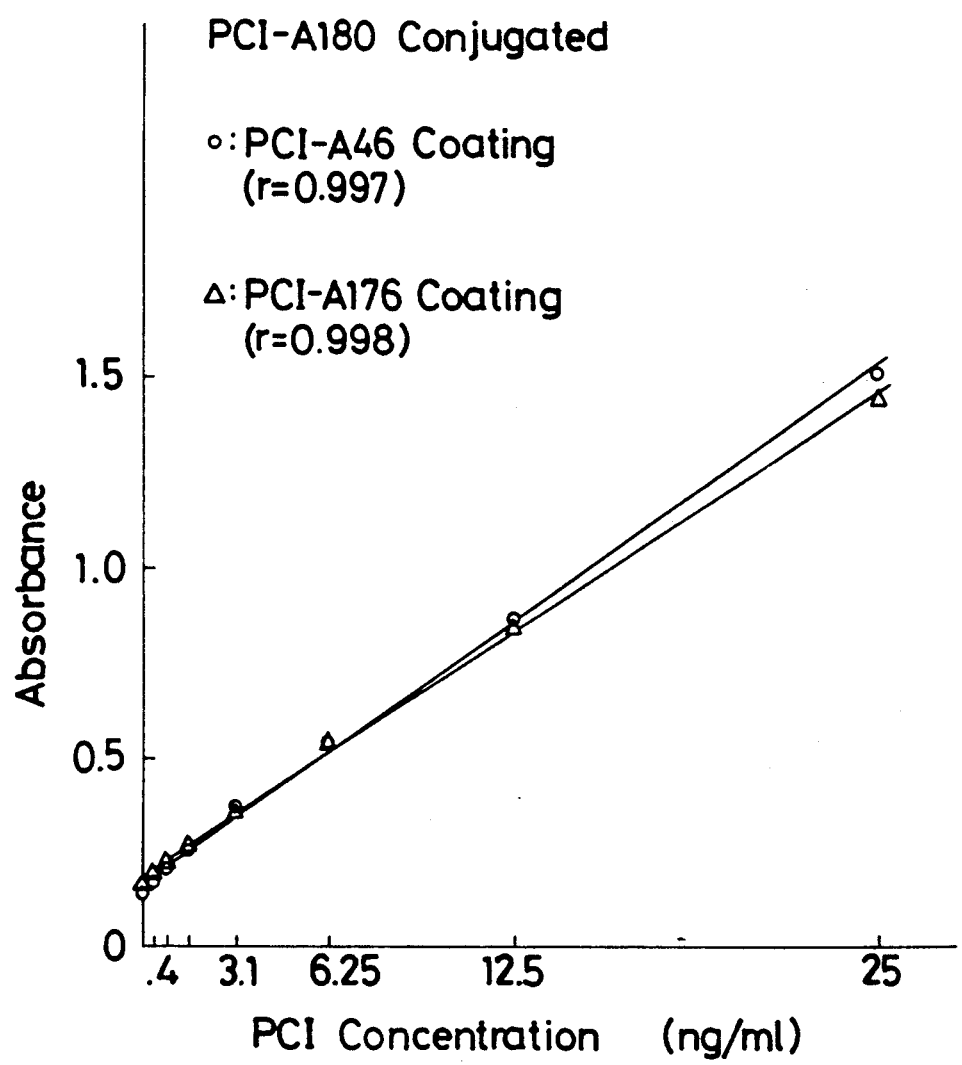
FIGS. 1 and 2 illustrate the absorbance (at 492 nm) as a function of the PCI concentration in the assay of PCI in Example 4.

The hybridoma secreting the monoclonal antibody specific to PCI can be formed, for example, in the following manner. (1) Antibody-secreting cells are prepared from an animal which has been immunized using PCI as an antigen. (2) Myeloma cells are prepared separately. (3) These cells are caused to fuse together. (4) The resulting hybridomas are allowed to grow selectively. (5) Antibody-secreting hybridomas are screened out from the hybridomas. (6) The intended hybridoma secreting the monoclonal antibody is obtained by cloning. Each of the above steps will next be described.

(1) Preparation of antibody-secreting cells

The preparation of antibody-secreting cells may be conducted in accordance with a method known commonly in the art. This may be done by immunizing an animal with PCI as an antigen and then collecting antibody-secreting cells from the animal. A mouse, rat, rabbit, guinea pig, sheep or the like may be mentioned by way of example as the animal. As the antibody-secreting cells, may be used those isolated from the spleen, lymph node, peripheral blood or the like. The immunization may be performed by a method in which the Freund's complete adjuvant is used in combination.

(2) Preparation of myeloma cells

No particular limitation is imposed on myeloma cells to be used in the cell fusion. Cell strains of many mammals may be used. It is however preferable to use the cell strains of an animal which belongs to the same family as the animal used for the preparation of the antibody-secreting cells. It is preferable to use a cell strain having specific chemical resistance, so that unfused cells and fused cells can be separated from each other after the cell fusion by incubating both unfused and fused cells in a selective medium in which unfused myeloma cells cannot survive but hybridomas alone are allowed to grow. For example, 8-azaguanine resistant cells are favorably employed because they cannot grow in HAT medium. As specific cell strains useful in the practice of this invention, may be mentioned mouse myeloma cell strains PAI, P3-X63-Ag8, P3-X63-Ag8-U1, P3-NSI/1-Ag4-1, X63-Ag8-6.5.3, SP2/0-Ag14, OF, S194/5XXO.BU.1, MPC11-45.6.TG.1.7, etc.

(3) Cell fusion

The cell fusion is effected usually by mixing myeloma cells and antibody-secreting cells (at a mixing ratio of 1:4–1:10, in general) in a medium such as MEM medium, PRMI1640 medium or IMDM medium. As a fusion promoter, may be used polyethylene glycol (PEG) the average molecular weight of which ranges from 1,000 to 6,000. PEG may be employed usually in an amount of 30–50%.

(4) Selective growth of hybridomas

Cells which have gone through the cell fusion are diluted suitably with IMDM medium containing 10% FCS or a like medium, followed by centrifugation. The resultant sediment is suspended in a selective medium (for example, HAT medium) and inoculated on a 96-well microtiter plate. It is then cultured in a 5% carbon dioxide culture apparatus. Cells which have grown in the selective medium are hybridomas.

(5) Screening of antibody-secreting hybridomas:

The screening of antibody-secreting hybridomas may be effected by a method known per se in the art. No particular limitation is imposed thereon. For example, the screening may be conducted by collecting a culture with hybridomas grown therein, reacting the hybridomas with PCI and then reacting the resultant product further with a second antibody labelled with an enzyme, fluorescent substance or light-emitting substance.

(6) Cloning

Cells in a culture well, which has been found to contain antibody-secreting hybridomas, are subjected to cloning in accordance-with the limiting-dilution method or the like, whereby a hybridoma secreting the monoclonal antibody is obtained.

Following the above-described procedures, were obtained hybridomas secreting a monoclonal antibody specific to PCI, i.e., hybridomas PCI-H39, PCI-H46, PCI-H167, PCI-H169, PCI-H176 and PCI-H180. These hybridomas are novel cells which can each secrete a monoclonal antibody specific to PCI. A procedure was therefore taken to deposit these cells with Fermentation Research Institute, Agency of Industrial Science and Technology, Government of Japan. Their deposit was however turned down by Notice of Refusal of Acceptance of Microorganism Deposit, Serial No. SHO 61-1415. On the other hand, Institute for Fermentation Osaka (IFO) accepted their deposit under IFO 50128 for hybridoma PCI-H39, IFO 50129 for hybridoma PCI-H46, IFO 50130 for hybridoma PCI-H167, IFO 50131 for hybridoma PCI-H169, IFO 50132 for hybridoma PCI-H176 and IFO 50133 for hybridoma PCI-H180.

The monoclonal antibody specific to PCI can be formed by using the antibody-secreting hybridoma obtained above. Namely, the monoclonal antibody of this invention can be obtained from a culture supernatant by culturing the antibody-secreting hybridoma in a suitable medium. In order to form the monoclonal antibody in a large volume, a mineral oil such as pristane (2,6,10,14-tetramethylpentadecane) is peritoneally administered to an animal of the same family as an animal used to obtain the myeloma cells and the antibody-secreting hybridoma is then inoculated, whereby the antibody-secreting hybridoma is allowed to grow in vivo to a large volume. According to the above-described method, the monoclonal antibody is formed at a high concentration in both serum and ascitic fluid of the inoculated animal. The separation and purification of the monoclonal antibody may be practised in accordance with a method which is used routinely for the purification of an antibody from serum.

The thus-obtained monoclonal antibody of this invention includes six types of monoclonal antibodies depending on the type of the antibody-secretin9 hybridoma employed, namely, PCI-A39, PCI-A46, PCI-A-167, PCI-A169, PCI-A176 and PCI-A180. These monoclonal antibodies have characteristics shown in Table 1, in which the molecular weights were measured by SDS-polyacrylamide gel electrophoresis, the isoelectric points by isoelectric point electrophoresis (an LKB-column isoelectric point electrophoretic apparatus), and the immunoglobulin subclasses by the Ouchterlony's double immunodiffusion test [a rabbit polyclonal antibody (product of Miles Laboratory) was used].

TABLE 1

| Hybridoma | Monoclonal antibody | Molecular weight | IgG sub-class | Isoelectric point |
| --- | --- | --- | --- | --- |
| PCI-H39 | PCI-A39 | 165,000 ± 5,000 | IgG 3 | 7.2–7.5 |
| PCI-H46 | PCI-A46 | 140,000 ± 5,000 | IgG 1 | 6.8–7.1 |
| PCI-H167 | PCI-A167 | 153,000 ± 5,000 | IgG 1 | 7.8–8.2 |
| PCI-H169 | PCI-A169 | 150,000 ± 5,000 | IgG 1 | 6.2–6.6 |
| PCI-H176 | PCI-A176 | 156,000 ± 5,000 | IgG 1 | 7.4–7.7 |
| PCI-H180 | PCI-A180 | 145,000 ± 5,000 | IgG 1 | 7.2–7.5 |

As described above, PCI is purified by using the monoclonal antibody of this invention as an immunoadsorbent. This may be practises, for example, by coupling the monoclonal antibody of this invention with a solid carrier such as dextran gel, agarose gel or polyvinyl gel and then subjecting crude PCI to chromatography on a column of the monoclonal antibody coupled carrier as an immunoadsorbent. The coupling of the solid carrier and monoclonal antibody is effected in accordance with the cyanogen bromide method or via epoxy, amino, carboxyl or formyl groups.

The crude PCI is charged into the column in which the solid carrier with the monoclonal antibody coupled thereon is packed. By eluting PCI adsorbed on the column, PCI can be obtained in a highly pure form.

The immunoassay of PCI, which makes use of the monoclonal antibodies of this invention, may be practised, for example, in the following manner. The monoclonal antibody of this invention is labelled with a labelling agent such as an enzyme, isotope or fluorescent substance. A PCI-containing sample is then added to the resultant conjugate. The degree of labelling of the immunoreaction product between the PCI and conjugate is thereafter measured. The ELISA method may also be used as a general method.

Having generally described the invention, a more complete understanding can be obtained by reference to certain specific examples, which are provided herein for purposes of illustration only and are not intended to be limiting unless otherwise specified.

EXAMPLES

This invention will hereinafter be described by the following Examples.

Example 1

Formation of hybridoma secreting anti-PCI monoclonal antibody:

(1) Purification of antigen (PCI)

(i) Five human placentae (about 2,500 g) were minced subsequent to removal of membranes and the like and thorough washing with a physiological saline. The thus-minced placentae were ground in a Waring blender and then added with Two liters of a 50 mM tris-hydrochloric acid buffer (pH 7.4), followed by further comminution in "Polytron". The resulting homogenate was subjected to centrifugal separation at 7,000 r.p.m. for 15 minutes to collect a sediment. Two liters of the 50 mM tris-hydrochloric acid buffer (pH 7.4) were added again to the thus-collected sediment, and the resulting mixture was homogenized in "Polytron" and then subjected to centrifugal separation at 7,000 r.p.m. for 15 minutes to obtain a washed sediment. The above procedure was repeated several times until blood components were removed to obtain about 930 g of a washed sediment finally.

(ii) About 2 liters of a 50 mM tris-hydrochloric acid buffer (pH 7.4) containing 50 mM of EDTA were added to 900 g of the sediment obtained in the above procedure (i), followed by homogenization in the Waring blender. The resulting homogenate was agitated overnight at 4° C., followed by centrifugal separation at 7,000 r.p.m. for 15 minutes to obtain 2 liters of an extract.

(iii) Solid ammonium sulfate was added to the extract obtained in the above (ii) to 35% of its saturated concentration. After allowing the resultant mixture to stand at 4° C. for 30 minutes to several hours, it was centrifuged at 7,000 r.p.m. for 15 minutes to collect a supernatant. Ammonium sulfate was added further to the supernatant to 85% of its saturated concentration. The resultant mixture was allowed to stand at 4° C. for 2 hours, followed by centrifugation at 7,000 r.p.m. for 15 minutes to collect a sediment. The thus-obtained sediment was dissolved in a small amount of a 20 mM tris-hydrochloric acid buffer and thoroughly dialyzed overnight at 4° C. against the same buffer. The precipitate formed during the dialysis was removed by centrifugation at 7,000 r.p.m. for 15 minutes to obtain 390 ml of a dialyzate.

(iv) The thus-obtained dialyzate was adsorbed on DEAE-Toyopearl (trade name; φ 5.5 × 1.9 cm) which had been equilibrated with a 20 mM tris-hydrochloric acid buffer (ph 7.4) and washed thoroughly with the same buffer. Using 4-liter portions of the same buffer which portions contained 0 to 0.3 M of sodium chloride respectively, elution was then performed at a rate of 20 ml per fraction in accordance with the linear concentration gradient method. Active fractions were eluted around a sodium chloride concentration of approximately 0.15 M, thereby containing 380 ml of active fractions.

(v) The resultant active factions were thoroughly dialyzed overnight at 4° C. against a 0.1 M phosphage buffer (pH 7.0) and the dialyzate was caused to pass through a column (φ2.5 cm × 12 cm) of "Blue Sepharose" was previously equilibrated with the same buffer. Column effluent fractions which showed an absorption of $A_{280}$ were collected and then concentrated through a "DIAFLOW Membrane Filter YM-10" (trade name).

(vi) The concentrate obtained in the above procedure (v) was subjected to gel filtration using "Sephadex G-100" (trade name; φ 4.5 × 75 cm) and eluted at a rate of 8 ml per fraction with a physiological saline. Active fractions 88-104 were collected and concentrated by ultrafiltration to obtain 4.5 ml of PCI (protein weight: 136.1 mg, Lowry method). The substantially pure, glucose-free polypeptide consists of the following amino acid sequence:

Further, the yields of proteins obtained in the respective purification stages will be described below.

(2) Preparation of immunized spleen cells

The above-purified PCI (100 μg) was emulsified in the Freund complete adjuvant and administered intraperitoneally to BALB/C mice.

PCI (50 μg/administration) and an adjuvant emulsion were thereafter administered twice at an interval of 2 weeks and finally, 50 μg of PCI was administered solely to complete the immunization.

Three days later, the mouse was sacrificed. After taking out the spleen and chopping same, it was filtered through a 100-mesh nylon mesh to obtain isolated spleen cells.

(3) Preparation of hybridoma

A hypotonic solution (155 mM ammonium chloride) was added to the thus-obtained immunized spleen cells to subject red blood cells to hemolysis. The cells were then washed three times with Iscove's modified Dulbecco's medium (IMDM). On the other hand, mouse myeloma cells PAI were also washed three times with IMDM. Both cells were counted. The spleen cells and PAI cells were combined together at a ratio of 5:1, followed by centrifugation. The supernatant was decanted out, and after loosening and separating the resultant cell sediment, 0.5 ml of a 45% solution obtained by diluting polyethylene glycol (PEG) 4,000 with a culture medium was added dropwise to effect fusion. After allowing the resultant mixture to stand at 37° C. for 30 seconds, 1 ml of IMDM was added gently over 1 minute. Thereafter, 10 ml of IMDM was added over 5 minutes to a final volume of 40 ml in a centrifugal tube. The centrifugal tube was centrifuged at 1,000 rpm for 8 minutes.

The resulting sediment was suspended in IMDM which had been added with 10% of fetal calf serum (FCS). The suspension was centrifuged again and the resultant supernatant was decanted out.

The thus-obtained sediment was suspended again in (HAT-)10% FCS-added IMDM in which $10^{-4}$ M of hypoxanthine, $4 \times 10^{-7}$ M of aminopterin and $1.6 \times 10^{-5}$ M of thymidine had been added in advance. The resultant suspension was poured in 100-μl portions into the individual wells of a 96-well microtiter plate. Each well was added with 50 μl of the medium every third-fourth day. Growth of cells was observed.

It was confirmed that hybridomas were only allowed to grow owing to the selective action of HAT.

(4) Screening of antibody-secreting hybridomas

The culture in a well, in which hybridomas had grown, was collected and a test was performed by enzyme immunoassay to determine if antibody-secreting hybridomas were contained there. First of all, PCI was poured at a rate of 0.1 μgu/100μl/well into each well of a 96-well microtiter plate ("Immunoplate I", trade name; product of NUNC Company). The microtiter plate was left over at 25° C. for 18 hours so as to adsorb PCI. Thereafter, a culture as a sample was poured at a rate of 100 μl/well to react at 25° C. for 2 hours. After washing the culture three times with a phosphate-buffered saline containing 0.05% of "Tween 20" (trade name) [PBS-Tween(trade mark)], horse radish peroxidase conjugated goat anti-mouse IgG (product of KPL Laboratories, Inc.) was added at a rate of 100 μl/well and two hours later, the culture was washed three times with PBS-Tween. Each well was then added with a 0.1 M citric acid-sodium hydroxide buffer (pH 5.0) containing 0.001% of hydrogen peroxide solution and 0.4 mg/ml; of orthophenylene diamine (product of Sigma Chemical Company) and the absorbance of the culture in each well was measured at a wavelength of 492 nm.

Since development of a stain was observed only in wells where an antibody to PCI existed, cells were collected from the wells which were stained.

(5) Cloning of hybridomas secreting a monoclonal antibody specific to PCI

Abdominal cells collected by injecting IMDM into the abdominal cavity of a mouse were used as feeder cells.

The abdominal cells suspended at $1 \times 10^5$ cells/ml in 10% FCS-added IMDM were poured in 100-μl portions into the individual wells of a 96-well microtiter plate. On the following day, antibody-secreting hybridomas were prepared at a concentration of 5 cells/ml and poured in 100-μl portions into the individual wells. Every third day, the culture medium was replaced by a fresh supply of the same medium, and culture supernatants were successively sampled out from wells in which hybridomas had grown to an appropriate volume. Confirmation of the secretion of the antibody was conducted by the same method as that described above. The cultures of positive wells were cloned again to obtain hybridomas secreting an anti-PCI monoclonal antibody. Six types of hybridomas were obtained. As already shown in Table 1, they were named PCI-H39, PCI-H46, PCI-H167, PCI-H169, PCI-H176 and PCI-H180 in accordance with the types of the anti-PCI monoclonal antibodies which they secrete respectively.

Example 2

Preparation of anti-PCI monoclonal antibody:

Seven-weeks-old BALB/C mice were intraperitoneally administered with 0.5 ml of pristane (product of Aldrich Chemical Co., Inc.). About one week later, the mice were intraperitoneally inoculated with the above-obtained hybridomas at a rate of $1 \times 10^6$ cells/mouse. About 10 days later, ascitic fluid was collected from the abdominal cavities of the mice. The fluid was centrifuged at 3,000 rpm for 10 minutes to collect a supernatant. Ammonium sulfate was added to 5 ml of the supernatant until the final concentration of ammonium sulfate reached 50% saturation. The resultant mixture was allowed to stand overnight at 4° C. The mixture was then centrifuged at 3,000 rpm for 15 minutes, and the resultant sediment was dissolved in a 0.1 M tris-hydrochloric acid buffer (pH 8) and thereafter dialyzed against the same buffer. The resulting dialyzate was subjected to chromatography on a column packed with "Protein A Sepharose CL-4B" (product of Pharmacia AB) which had been equilibrated with the same buffer.

The elution of the monoclonal antibody was conducted with a 0.1 M glycin-0.15 M sodium chloride buffer (pH 2.7), whereby the anti-PCI monoclonal antibody was obtained. When PCI-H39 was used, 14.2 mg of PCI-A39 was obtained. 20.2 mg of PCI-A46 from PCI-H46, 22.9 mg of PCI-A167 from PCI-H167, 25.0 mg of PCI-A169 from PCI-H169, 25.0 mg of PCI-A176 from PCI-H176, and 8.6 mg of PCI-A180 from PCI-H180. Those anti-PCI monoclonal antibodies exhibited the characteristics shown above in Table 1.

Example 3

Purification of PCI by immune affinity chromatography:

(1) Coupling of the anti-PCI monoclonal antibody to carrier

Cyanogen-bromide-activated Sepharose 4B (0.4 g) was washed successively with 1 mM hydrochloric acid and a 0.1 M sodium bicarbonate-0.5 M sodium chloride buffer (pH 8.3) to prepare 1.5 ml of a coupling buffer of cyanogen-bromide-activated Sepharose 4B.

A matching coupling buffer (1 ml) of 2 mg of the purified monoclonal antibody PCI-A46 was added to the former coupling buffer. The resultant mixture was shaken for 2 hours at room temperature and was then dewatered through a glass filter. Ten milliliters of a 0.1 M tris-hydrochloric acid buffer (pH 8.0) were added further and the resultant mixture was shaken for 2 hours at room temperature to block any remaining active sites.

The thus-obtained antibody-conjugated Sepharose 4B was washed three times alternately with a 0.1 M tris-hydrochloric acid-0.5 M sodium chloride buffer (pH 8.3) and a 0.1 M acetic acid-0.5 M sodium chloride buffer (pH 4.0), followed by equilibration with a 0.1 M tris-hydrochloric acid buffer (pH 7.4) to obtain an antibody column 46.

Purification of PCI by the antibody column

The crude PCI solution obtained in Example 1-(i)-(ii) was charged into the antibody column 46 prepared in the above procedure. The column was washed thoroughly with the same buffer as that employed for its equilibration.

The elution of PCI can be effected with a 0.1 M acetic acid-0.5 M sodium chloride buffer (pH 5.0) or with a 0.1 M tris-hydrochloric acid-0.1 M calcium chloride (pH 7.4).

PCI was not found in any through fractions. PCI was obtained in a pure form at a recovery rate of at least 70% from eluate fractions.

Incidentally, data such as purification coefficient are shown in Table 2. The measurement of PCI was conducted by a method to be described subsequently in Example 4.

TABLE 2

| | Protein weight (µg) | PCI (µg) | Yield (%) | Purification coefficient |
|---|---|---|---|---|
| Crude PCI solution charged into column | 1507 | 44.6 | 100 | 1.0 |
| Through fractions | 1433 | N.D.* | — | — |
| Eluate 0.1M acetate-0.5M NaCl buffer (pH 5) | 40.6 | 31.4 | 70.5 | 26.2 |
| Crude PCI solution charged into column | 1004 | 29.6 | 100 | 1.0 |
| Through fractions | 969 | N.D. | — | — |
| Eluate 0.1M Tris-HCl-0.1M CaCl₂ buffer (pH 7.4) | 30 | 21.7 | 73.3 | 24.6 |

*N.D.: Not detected.

Example 4

PCI assay making use of anti-PCI monoclonal antibody:

Following the procedure reported by S. Yoshitake et al. [J. Biochem, 92, 1413-1424 (1982)], horse radish peroxidase (hereinafter abbreviated as "HRP") was conjugated with the anti-PCI monoclonal antibody. Using the resultant HRP-conjugated anti-PCI monoclonal antibody, PCI was measured by the ELISA method in the following manner. A solution of the monoclonal antibody in a 0.05 M sodium carbonate solution (pH 9.6) was added in 100-µl portions into the individual wells of a 96-well flat-bottom microtiter plate and the walls of the wells were coated with the antibody at 25° C. for 2 hours. After washing the wells with PBS-Tween (trade name), 100 µl of a solution of a sample in a 0.1 M Tris-HC1-25 mM EDTA-0.05% "Tween 20" (trade name) buffer (pH 7.4) was added to each of the wells. After reacting the antibody and sample overnight at 25° C., each well was washed with PBS-Tween and then added with 100 µl of a diluted solution of the HRP-conjugated monoclonal antibody in PBS-Tween, followed by a reaction at 25° C. for 2 hours. After washing each well with PBS-Tween, each well was added with 100 µl of a substrate solution (a 0.1 M citrate-phosphate buffer containing 0.4 mg/ml of ortho-phenylenediamine and 0.01% of hydrogen peroxide; pH 5.0), followed by a further reaction at 25° C. for 30 minutes. Fifty microliters of 4.5 M sulfuric acid were added to terminate the reaction and the absorbance at 492 nm was measured. Results are shown in Table 3.

TABLE 3

| | Coating monoclonal antibody | | | | | |
|---|---|---|---|---|---|---|
| | PCI-A39 | PCI-A46 | PCI-A167 | PCI-A169 | PCI-A176 | PCI-A180 |
| Enzyme-conjugated monoclonal antibody | | | | | | |

TABLE 3-continued

|  | Coating monoclonal antibody | | | | | |
|---|---|---|---|---|---|---|
|  | PCI-A39 | PCI-A46 | PCI-A167 | PCI-A169 | PCI-A176 | PCI-A180 |
| PCI-A39 | 3 | 1 | 3 | 2 | 2 | 2 |
| PCI-A46 | 2 | 3 | 3 | 2 | 1 | 2 |
| PCI-A167 | 3 | 3 | 3 | 3 | 3 | 3 |
| PCI-A169 | 2 | 1 | 3 | 3 | 2 | 2 |
| PCI-A176 | 2 | 1 | 3 | 2 | 3 | 2 |
| PCI-A180 | 2 | 1 | 3 | 2 | 1 | 3 |

1: successfully,
2: not successfully applicable,
3: inapplicable.

Figure 2:
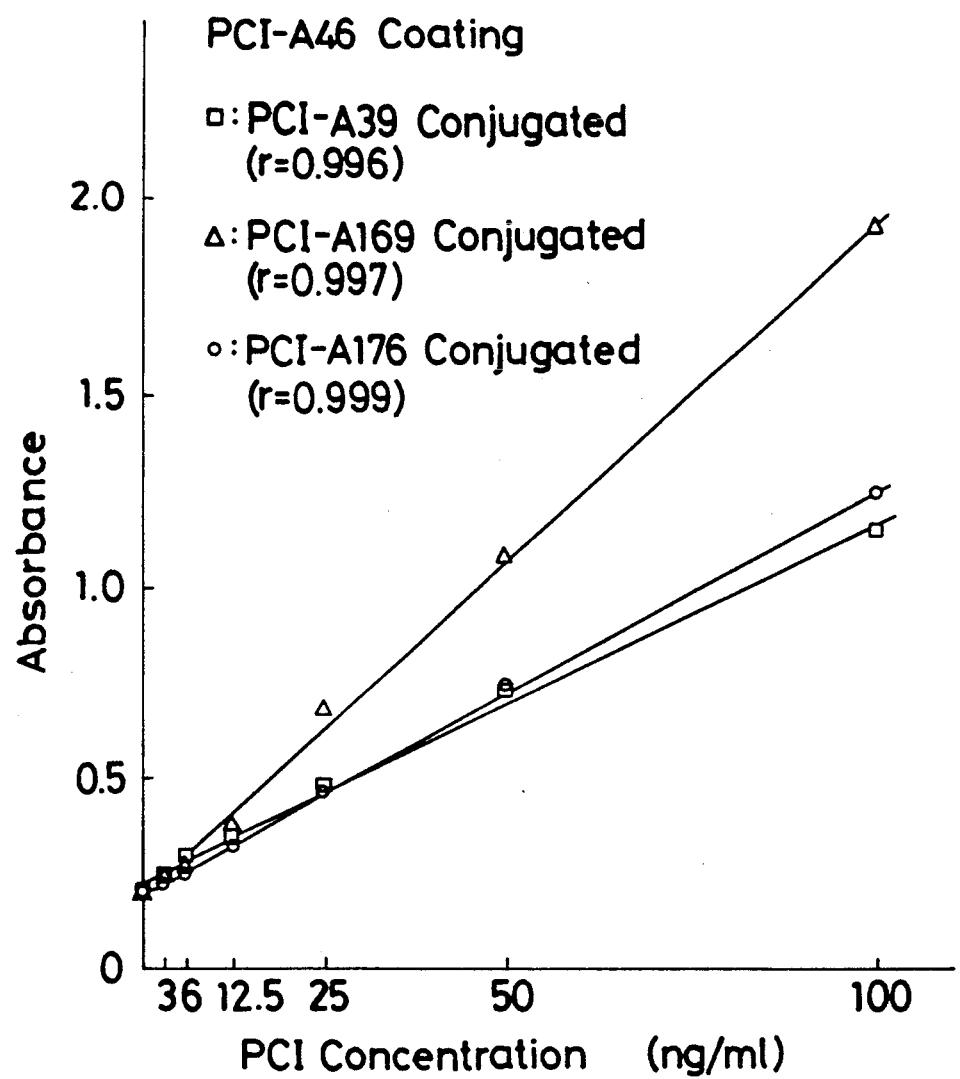

Calibration curves obtained when PCI-A46 and 176 were used separately as coating monoclonal antibodies and PCI-A180 was used commonly as a monoclonal antibody to be conjugated had extremely high sensitivity and moreover exhibited good linearity as illustrated in FIG. 1. In addition, calibration curves obtained when PCI-A46 was used commonly as a coating monoclonal antibody and PCI-A39, 169 and 176 were employed separately as monoclonal antibodies to be conjugated also showed good linearity as depicted in FIG. 2.

PCI in a concentration range of 5-100 ng/ml has been found detectable as shown in Table 3 when PCI-A46 is used as a coating monoclonal antibody and PCI-A39, 169, 176 or 180 is used as a monoclonal antibody to be conjugated or when PCI-A176 is used as a coating monoclonal antibody and PCI-A46 or 180 is used as a monoclonal antibody to be conjugated.

Having now fully described the invention, it will be apparent to one of ordinary skill in the art that many changes and modifications can be made thereto without departing from the spirit or scope of the invention as set forth herein.

We claim:

1. A substantially pure, glucose-free polypeptide consisting of the following amino acid sequence:

Ala—Gln—Val—Leu—Arg—Gly—
—Thr—Val—Thr—Asp—Phe—Pro
Gly—Phe—Asp—Glu—Arg—Ala—
—Asp—Ala—Glu—Thr—Leu—Arg
Lys—Ala—Met—Lys—Gly—Leu—
—Gly—Thr—Asp—Glu—Glu—Ser
Ile—Leu—Thr—Leu—Leu—Thr—
Ser—Arg—Ser—Asn—Ala—Gln
Arg—Gln—Glu—Ile—Ser—Ala—
—Ala—Phe—Lys—Thr—Leu—Phe
Gly—Arg—Asp—Leu—Leu—Asp—
—Asp—Leu—Lys—Ser—Glu—Leu
Thr—Gly—Lys—Phe—Glu—Lys—
—Leu—Ile—Val—Ala—Leu—Met
Lys—Pro—Ser—Arg—Leu—Tyr—

-continued

—Asp—Ala—Tyr—Glu—Leu—Lys
His—Ala—Leu—Lys—Gly—Ala—
—Gly—Thr—Asn—Glu—Lys—Val
Leu—Thr—Glu—Ile—Ile—Ala—
—Ser—Arg—Thr—Pro—Glu—Glu
Leu—Arg—Ala—Ile—Lys—Gln—
—Val—Tyr—Glu—Glu—Glu—Tyr
Gly—Ser—Ser—Leu—Glu—Asp—
—Asp—Val—Val—Gly—Asp—Thr
Ser—Gly—Tyr—Tyr—Gln—Arg—
—Met—Leu—Val—Val—Leu—Leu
Gln—Ala—Asn—Arg—Asp—Pro—
—Asp—Ala—Gly—Ile—Asp—Glu
Ala—Gln—Val—Glu—Gln—Asp—
—Ala—Gln—Ala—Leu—Phe—Gln
Ala—Gly—Glu—Leu—Lys—Trp—
—Gly—Thr—Asp—Glu—Glu—Lys
Phe—Ile—Thr—Ile—Phe—Gly—
—Thr—Arg—Ser—Val—Ser—His
Leu—Arg—Lys—Val—Phe—Asp—
—Lys—Tyr—Met—Thr—Ile—Ser
Gly—Phe—Gln—Ile—Glu—Glu—
—Thr—Ile—Asp—Arg—Glu—Thr
Ser—Gly—Asn—Leu—Glu—Gln—
—Leu—Leu—Leu—Ala—Val—Val
Lys—Ser—Ile—Arg—Ser—Ile—
—Pro—Ala—Tyr—Leu—Ala—Glu
Thr—Leu—Tyr—Tyr—Ala—Met—
—Lys—Gly—Ala—Gly—Thr—Asp
Asp—His—Thr—Leu—Ile—Arg—
—Val—Met—Val—Ser—Arg—Ser
Glu—Ile—Asp—Leu—Phe—Asn—
—Ile—Arg—Lys—Glu—Phe—Arg
Lys—Asn—Phe—Ala—Thr—Ser—
—Leu—Tyr—Ser—Met—Ile—Lys
Gly—Asp—Thr—Ser—Gly—Asp—
—Tyr—Lys—Lys—Ala—Leu—Leu
Leu—Leu—Cys—Gly—Glu—Asp—Asp.

* * * * *

UNITED STATES PATENT AND TRADEMARK OFFICE
CERTIFICATE OF CORRECTION

PATENT NO. : 5,290,915
DATED : March 1, 1994
INVENTOR(S) : Hiroshi NAKAO, et al.

It is certified that error appears in the above-indentified patent and that said Letters Patent is hereby corrected as shown below:

On the title page, Item [*], the Terminal Disclaimer Date
should read as follows:

--Mar. 22, 2005--

Signed and Sealed this

Twelfth Day of July, 1994

Attest:

BRUCE LEHMAN

*Attesting Officer*    *Commissioner of Patents and Trademarks*